(12) United States Patent  
Djakov

(10) Patent No.: US 8,881,578 B2  
(45) Date of Patent: Nov. 11, 2014

(54) FLUID PROBE

(75) Inventor: Vladislav Djakov, Abingdon (GB)

(73) Assignee: Microvisk Ltd., St. Asaph (GB)

(*) Notice: Subject to any disclaimer, the term of this patent is extended or adjusted under 35 U.S.C. 154(b) by 1310 days.

(21) Appl. No.: 12/673,052

(22) PCT Filed: Aug. 8, 2008

(86) PCT No.: PCT/GB2008/002717  
§ 371 (c)(1),  
(2), (4) Date: Dec. 19, 2011

(87) PCT Pub. No.: WO2009/022121  
PCT Pub. Date: Feb. 19, 2009

(65) Prior Publication Data  
US 2012/0090387 A1   Apr. 19, 2012

(30) Foreign Application Priority Data  
Aug. 11, 2007 (GB) .................................. 0716202.7

(51) Int. Cl.  
*G01N 11/10* (2006.01)  
*G01N 11/16* (2006.01)

(52) U.S. Cl.  
CPC .................................... *G01N 11/16* (2013.01)  
USPC ...................................................... 73/54.24

(58) Field of Classification Search  
USPC ............................................. 73/54.24–54.34  
See application file for complete search history.

(56) References Cited

U.S. PATENT DOCUMENTS 3,282,084 A  11/1966 Banks  
4,695,956 A   9/1987 LeVeen et al.

(Continued)

FOREIGN PATENT DOCUMENTS

DE   10029091   1/2002  
EP    1674865   6/2006

(Continued)

OTHER PUBLICATIONS

Thaysen, J. et al., "SU-8 Based Piezoresistive Mechanical Sensor," The Fifteenth IEEE International Conference on Micro Electro Mechanical Systems, 2002, Las Vegas, pp. 320-323.

(Continued)

*Primary Examiner* — John Fitzgerald  
(74) *Attorney, Agent, or Firm* — Douglas G. Gallagher; John V. Daniluck; Bingham Greenebaum Doll LLP

(57) ABSTRACT

Device and associated methods for detecting a property of a fluid. The device includes a body region and a first flexible element having a first end and a second end. The first end is fixedly located on the body region. The flexible element includes at least a first layer having a first coefficient of thermal expansion and a second layer having a second, different coefficient of thermal expansion. An electrical heater element can be arranged to heat the flexible element to induce bending of said flexible element. The resistance of a first portion of the electrical heater element adjacent the first end can be greater than the resistance of a second portion of the electrical heater element further from the first end. The device can include a heater controller arranged to supply an electrical pulse having a duration less than 5 ms to the electrical heater. The device can include a second, reference flexible element having a first end and a second end, with the first end fixedly located on the body region. Each flexible element can include a respective sensor arranged to provide a signal indicative of the movement of that flexible element. The sensor of the reference flexible element has a different configuration than the sensor of the first flexible element, with at least one of the flexible elements including at least one additional portion of material for equalizing the thermal conductivity distribution of the two flexible elements.

24 Claims, 13 Drawing Sheets

(56) References Cited

U.S. PATENT DOCUMENTS

| | | |
|---|---|---|
| 5,771,902 A | 6/1998 | Lee et al. |
| 5,780,727 A | 7/1998 | Gimzewski et al. |
| 6,044,694 A | 4/2000 | Anderson et al. |
| 6,182,499 B1 | 2/2001 | McFarland et al. |
| 6,249,001 B1 | 6/2001 | Sauer et al. |
| 6,260,408 B1 | 7/2001 | Vig et al. |
| 6,269,685 B1 | 8/2001 | Oden |
| 6,269,686 B1 | 8/2001 | Hahn et al. |
| 6,311,549 B1 | 11/2001 | Thundat et al. |
| 6,436,647 B1 | 8/2002 | Quate et al. |
| 6,457,360 B1 | 10/2002 | Daraktchiev et al. |
| 6,575,020 B1 | 6/2003 | de Charmoy Grey et al. |
| 6,679,055 B1 | 1/2004 | Ellis |
| 6,715,339 B2 * | 4/2004 | Bonne et al. ............ 73/24.01 |
| 7,047,794 B2 | 5/2006 | Hajduk et al. |
| 2003/0056574 A1 | 3/2003 | Drahm et al. |
| 2003/0062193 A1 | 4/2003 | Thaysen et al. |
| 2007/0033990 A1 | 2/2007 | Grey et al. |
| 2007/0272002 A1 | 11/2007 | Jakoby |
| 2008/0011058 A1 | 1/2008 | Lal et al. |

FOREIGN PATENT DOCUMENTS

| | | |
|---|---|---|
| GB | 2359368 | 8/2001 |
| GB | 2369887 | 6/2002 |
| JP | 2001150393 | 6/2001 |
| WO | 9502180 | 1/1995 |
| WO | 9947908 | 9/1999 |
| WO | 0066266 | 11/2000 |
| WO | 0212443 | 2/2002 |
| WO | 0039537 | 7/2002 |
| WO | 03022731 | 3/2003 |
| WO | 03062135 | 7/2003 |
| WO | 03067248 | 8/2003 |
| WO | 03071258 | 8/2003 |
| WO | 03104784 | 12/2003 |
| WO | 2004059306 | 7/2004 |
| WO | 2004083802 | 9/2004 |
| WO | 2005054817 | 6/2005 |
| WO | 2007104978 | 9/2007 |
| WO | 2009022121 | 2/2009 |

OTHER PUBLICATIONS

PCT/JP2005/008755, International Preliminary Report on Patentability, dated Nov. 14, 2006.

Que et al., "Bent-Beam Electrothermal Actuators—Part I: Single Beam and Cascaded Devices," Journal of Microelectromechanical Systems, vol. 10, No. 2, pp. 247-254 [Actual Date Jun. 2001]. Jun. 30, 2001.

Djakov, V. et al., Bimorph Actuators for MOEMS, Proc. SPIE vol. 4755, pp. 804-814, Design, Test, Integration, and Packaging of MEMS/MOEMS [Actual Date 2002]. Dec. 31, 2002.

Coutinho, M.G. et al., "The Intelligent Motion Surface: A hardware/software tool for the assembly of meso-scale devices," IEEE International Conference on Robotics, and Automation, Albuquerue, NM [Actual Date 1997]. Dec. 31, 1997.

Suh, J.W. et al., "Organic thermal and electrostatic ciliary microactuator array for object manipulation," Sensors and Actuators A58, pp. 51-60 [Actual Date 1997]. Dec. 31, 1997.

Riethmuller, W. et al., "Thermally Excited Silicon Microactuators," IEEE Transactions on Electron Devices, vol. 35: No. 6, [Actual Date June 1988]. Jun. 30, 1988.

Ataka, M. et al., "Fabrication and Operation of Polymide Bimorph Actuators for a Ciliary Motion System," Journal of Microelectromechanical Systems, vol. 2: No. 4, pp. 146-150 [Actual Date Dec 1993]. Dec. 31, 1993.

* cited by examiner

FLUID PROBE

The present invention relates to a probe for the determination of a property of fluid, and to methods of manufacture and use of such probes. Embodiments of the present invention are suitable for, although not restricted to, the determination of the viscosity of fluids such as blood, and in particular for monitoring the change in viscosity (e.g. due to clotting) of such fluids as a function of time.

Sensors are known that use microscopic flexible mechanical structures, such as micro-cantilevers, micro-bridges or micro-membranes integrated into microscopic chambers. For example, U.S. Pat. No. 6,575,020 describes how various micro-cantilevers can be integrated into microscopic chambers. Changes in the mechanical properties of microscopic micro-cantilevers can be used to detect changes in the environment of the micro-cantilever. U.S. Pat. No. 6,575,020 describes how such micro-cantilevers are typically of the order of 100 microns long, 10 microns wide, and 1 micron thick, and can be made of materials such as silicon, silicon nitride, glass, metal or a combination of such materials. Such sensors may comprise an actuator for moving the cantilever relative to the interaction chamber. The actuator may be implemented in several ways e.g. by piezoelectric elements, means for providing an electrostatic or magnetic induced movement, or means providing a thermal induced movement, such as a heater element of the micro-cantilever.

One disadvantage of such micro-cantilever arrangements is that the cantilever is formed of a relatively rigid material, thus limiting the deflection range (and hence potential sensitivity) of the sensor.

International Patent Application No. PCT/GB2004/005079, published as WO 2005/054817, describes a device having a flexible element for detecting a property of a fluid. The flexible element can be formed of materials such as polymers, which are relatively flexible compared to silicon. The flexible element is between 100 micron and 1 mm in length, and can be bent between two configurations, with a corresponding movement of an end of the flexible element over a distance of between 30 micron and 650 micron. The flexible element is formed of two layers having different coefficients of thermal expansion. A heater is incorporated into the flexible element, to move the element from the first configuration to the second configuration. When the heat is removed, the element then relaxes back to the first configuration. An appropriate piezoresistive material can be used to determine the degree or rate of deflection of the element. FIG. 4 of WO 2005/54817 illustrates a square-wave pulse sequence that can be applied to the heater to drive the element, and the subsequent resulting change in resistance of the piezoresistive sensor element.

It is an aim of embodiments of the present invention to address one or more problems with the prior art, whether referred to herein or otherwise.

In a first aspect, the present invention provides a device for detecting a property of a fluid, comprising: a body region; a first flexible element having a first end and a second end, said first end being fixedly located on said body region, the first flexible element comprising at least a first layer having a first coefficient of thermal expansion and a second layer having a second, different coefficient of thermal expansion, and an electrical heater arranged to heat the flexible element to induce bending of said element, wherein the device may further comprise a heater controller arranged to supply an electrical pulse having a duration less than 8 ms to said electrical heater.

A pulse having a duration less than 8 ms is particularly suitable for use in measuring the properties of fluids, including liquids such as blood, water and glycerol, particularly in determining the viscosity of such fluids. The pulse results in measurable mechanical bending (including unbending) of the flexible element being temporally separate from the heat pulse used to cause the flexible element to bend. Such a short pulse can lead to the flexible element continuing to bend after the electrical pulse used to power the heater has been removed. Measurement, or sensing, of the mechanical bending may include sensing properties of the mechanical bending when the bending reaches a peak amplitude. The measurement may include measurements of properties of the peak amplitude such as the timing of the peak amplitude or the size of the peak amplitude of bending.

Further, such a short pulse can lead to a measurable mechanical oscillation, in which the flexible element oscillates as it unbends. In such a measurable mechanical oscillation, a relatively small amplitude of mechanical oscillation is superimposed upon the longer time period movement of the flexible element as it moves from the unbent to the bent position and back (as the element heats and subsequently cools). While a longer pulse would also generate mechanical oscillations in the flexible element, the oscillations would be very difficult to read in the presence of the continued heating of the flexible element. Hence, it is desirable that the heating pulse ends before the measurement of mechanical oscillations begins. The mechanical oscillation of the flexible element provides at least one extra parameter, in addition to the rate at which the sensor unbends, that can be fitted or otherwise analysed or determined to obtain parameters (e.g. viscosity) of the fluid surrounding the flexible element. In some cases, at least one measurement may be made of the rate of bending, or of the time taken to reach an extreme deflection during a mechanical oscillation, or a measurement may be made of the extent of bending during a mechanical oscillation.

It is not necessary to generate a plurality of pulses which occur in phase with the resonant frequency of the flexible element. The pulses may be generated at arbitrary timings relative to one another and do not need to be temporally linked (i.e. the pulses are temporally separate and do not need to occur at regular intervals or according to any repeating pattern).

The duration of the pulse may be less than 5 ms. The pulse may be sufficiently short in duration that the mechanical oscillation of the flexible element is distinguishable from bending due to the temperature of the flexible element.

The duration of the electrical pulse may be less than 1.5 ms. The duration of the electrical pulse may be less than 1 ms. The duration of the electrical pulse may be greater than 100 µs. It may be desirable for the pulse to be no less than 50 µs, for example in the case that a gas surrounds the flexible element. The controller may be arranged to supply a series of the electrical pulses, at a frequency at least two orders of magnitude lower than the resonant frequency of the flexible element. For example, the series of pulses may be generated at a frequency of less than 100 Hz. A duty cycle of for example 5%, 10% or 20% may be used.

The pulse duration and the rate of thermal expansion of said first and second layers may be such that the flexible element continues bending after the pulse.

The pulse duration and the pulse energy may be such that the flexible element bends an additional 50% after the pulse.

The pulse may be sufficiently short in duration that effective heating of the flexible element is achieved without significant heating of the environment around the flexible element. The pulse may be sufficiently long in duration that enough energy, in the form of heat, is transferred to the flexible element to cause the desired degree of bending without overheating any part of the device such that the device is damaged.

The minimum energy provided to the flexible element in the form of heat may be 1 µJ, for example if a gas surrounds the flexible element. The minimum energy provided to the flexible element in the form of heat may be 50 µJ, for example if a fluid of 1 centipoise surrounds the flexible element. The minimum energy provided to the flexible element in the form of heat may be 100 µJ, for example if a fluid of greater than 2 centipoise surrounds the flexible element. The minimum energy provided to the flexible element may be sufficient that the flexible element is caused to bend and experience a measurable mechanical overshoot.

The maximum energy provided to the flexible element in the form of heat may be 10 µJ, for example if a gas surrounds the flexible element. The maximum energy provided to the flexible element in the form of heat may be 60 µJ, for example if a fluid of 1 centipoise surrounds the flexible element. The maximum energy provided to the flexible element in the form of heat may be 150 µJ, for example if a fluid of greater than 2 centipoise surrounds the flexible element. The maximum energy provided to the flexible element in the form of heat may be 250 µJ. The maximum energy provided to the flexible element in the form of heat should not be sufficient to damage the flexible element or to cause the thermal bending of the flexible element to mask the mechanical overshoot produced by the bending.

The device may further comprise a sensor arranged to provide a signal indicative of the movement of the first flexible element.

In a second aspect, the present invention provides a method of operating a device for detecting a property of a fluid, the device comprising a body region; a first flexible element having a first end and a second end, said first end being fixedly located on said body region, the flexible element comprising at least a first layer having a first co-efficient of thermal expansion and a second layer having a second, different co-efficient of thermal expansion, and an electrical heater arranged to heat the flexible element to induce bending of said element, the method comprising providing an electrical pulse having a duration less than 8 ms to said electrical heater to induce bending of said element.

The electrical pulse may have a duration less than 5 ms. The method may further comprise sensing the movement of said flexible element, and thereby determining a value indicative of the viscosity of a fluid surrounding the flexible element. The magnitude of movement of the flexible element at a particular point during the motion of the flexible element may be sensed. This may comprise elements of thermally induced movement and mechanical movement. Alternatively, the time taken for the flexible element to complete a predetermined movement after the provision of the electrical pulse may be sensed. Such a movement may be movement of the flexible element to an extreme position, and then movement back towards an equilibrium position, such as from a mechanical oscillation.

The method may further comprise tracking the movement of the element to obtain data indicative of the movement over a period of time, and using the data to determine at least one value indicative of the viscosity of a fluid surrounding the flexible element.

In a third aspect, the present invention provides a device for detecting a property of a fluid, comprising: a body region; a first flexible element having a first end and a second end, said first end being fixedly located on said body region; a second, reference flexible element having a first end and a second end, said first end being fixedly located on said body region; each flexible element comprising at least a first layer having a first coefficient of thermal expansion and a second layer having a second, different coefficient of thermal expansion, and a respective sensor arranged to provide a signal indicative of the movement of the respective flexible element, wherein the sensor of the reference flexible element has a different configuration than the sensor of the first flexible element, with at least one of the flexible elements including at least one additional portion of material for equalising the thermal conductivity distribution of said flexible elements.

To ensure the temperature response of both the first and second flexible elements are similar, one or more additional portions of material can be provided within either one (or both, as appropriate) of the flexible elements. Equalising the thermal conductivity distribution (i.e. the distribution of the materials having particular thermal conductivity values or characteristics) within each flexible element will result in each flexible element having a roughly uniform temperature distribution when heated to the same degree, with similar heat exchange properties, despite the flexible elements having different configurations of sensors. Thus, the second flexible element can better act as a reference to the first flexible element.

The at least one additional portion of material may have a similar thermal conductivity to the sensors.

The at least one portion may be formed of the same material as the sensors.

The sensors may be formed of a thermal conductor.

Each sensor may comprise a metal.

The at least one additional portion of material may also be formed of a metal, and the ratio between the metal and non-metal constituents of each flexible element may be substantially the same.

The sensor of the second, reference flexible element may be configured to be less sensitive to mechanical strain caused by bending of the respective element than the sensor in the first flexible element.

The first flexible element may be located within a first flexible member, and the second flexible element may be located within a separate second flexible member.

The first and second flexible elements may be located within a single flexible member.

The sensor may comprise constantan.

The device may further comprise a processor arranged to process the signal from the sensor of the first flexible element, to provide a signal indicative of the viscosity of a medium surrounding said first flexible element.

The first flexible element may have a spring constant of less than 1 N/m.

The first flexible element may be between 10 microns and 2 mm in length from said first end to said second end.

The difference between the thermal expansion coefficients of said layers may be at least $10 \times 10^{-6}/°$ C.

The ratio between the thermal expansion coefficient of the first layer and the second layer may be at least 10.

The layers may be formed of materials having a Young's modulus less than 10 GPa.

In a fourth aspect, the present invention provides a device for detecting a property of a fluid, comprising: a body region; a first flexible element having a first end and a second end, said first end being fixedly located on said body region, the flexible element comprising at least a first layer having a first coefficient of thermal expansion and a second layer having a second, different coefficient of thermal expansion, and an electrical heater element arranged to heat the flexible element to induce bending of said flexible element, wherein the resistance of a first portion of the heater element adjacent the first end is greater than the resistance of a second portion of the heater element further from the first end, such that in use a first section of the flexible element comprising the first portion of the heater element receives more heat per unit time from the heater element than a second section of the flexible element comprising the second portion of the heater element, the second section having equal dimensions to the first section.

Providing a heater element having such a configuration ensures that greater heating of the flexible element occurs in a section close to the first end i.e. to the point at which the flexible element is connected to the body region. Thus, the deflection of the flexible element in that region can be maximised, resulting in overall greater deflection of the flexible element than would otherwise occur, and allowing greater device sensitivity.

Said first portion of the heater element could have a smaller cross-section than the second portion of the heater element. Said first portion of the heater element could be longer than said second portion of the heating element.

Said first portion may be located in an intermediate section of the flexible element between the first end and the second end.

Said first portion may be at the first end of the flexible element.

At least a further portion of the heater element located in an intermediate section of the flexible element between the first end and the second end, may have a smaller cross-section than the second portion of the heater element.

The heater element may be formed of a material having a substantially uniform resistivity.

The heater element may taper from a larger portion cross-section to a smaller portion cross-section.

In a fifth aspect, the present invention provides a method of manufacturing a device for detecting a property of a fluid, the method comprising forming a device as claimed in any one of the above claims, by providing the constituent parts of said device.

Embodiments of the present invention will now be described, by way of example only, with reference to the accompanying drawings, in which.

Figure 6A:
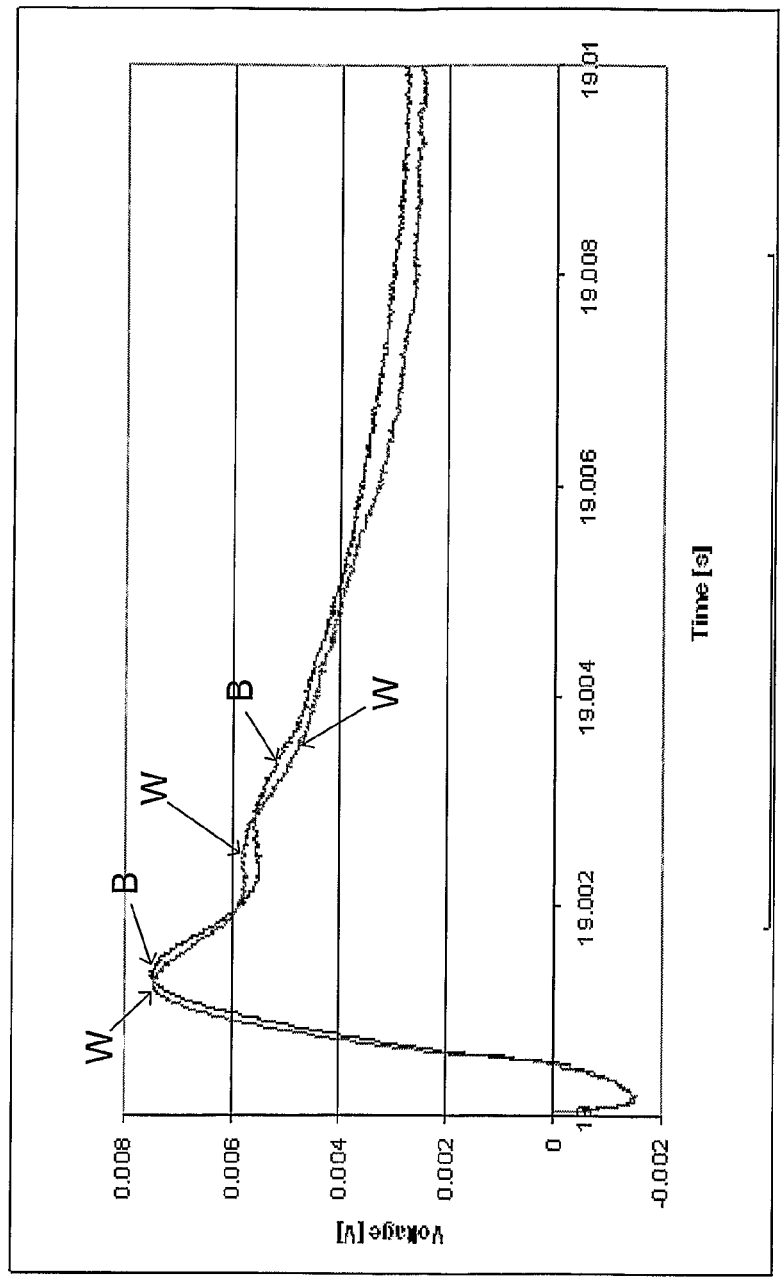
Figure 6B:
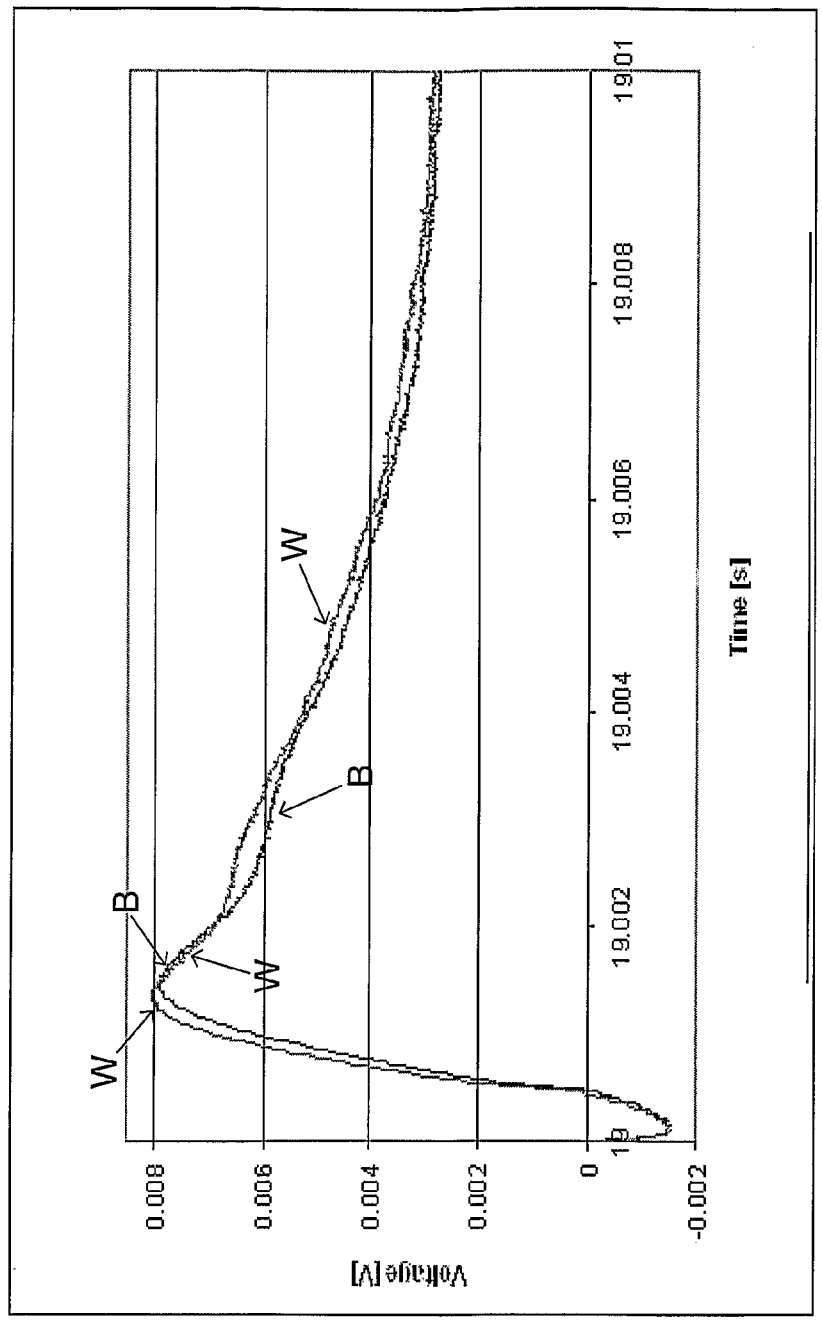
Figure 7:
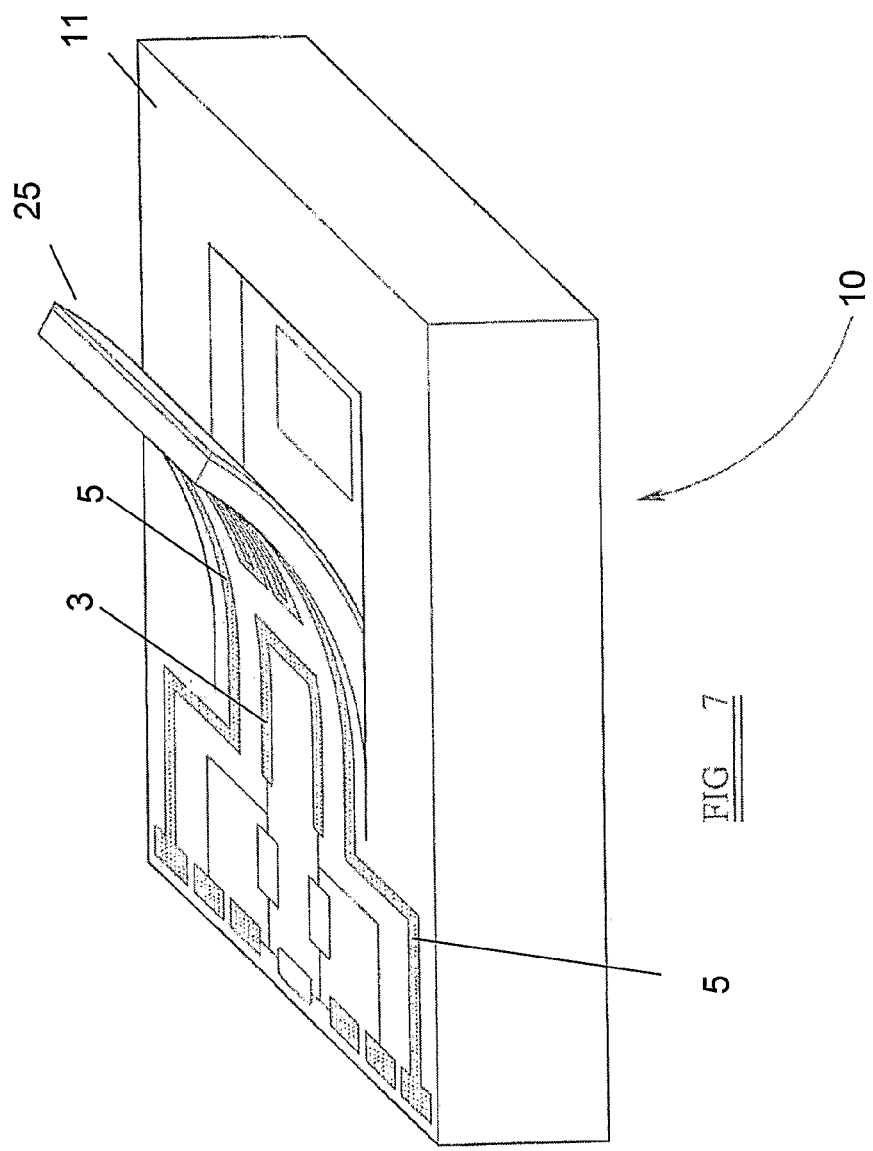
Figure 8:
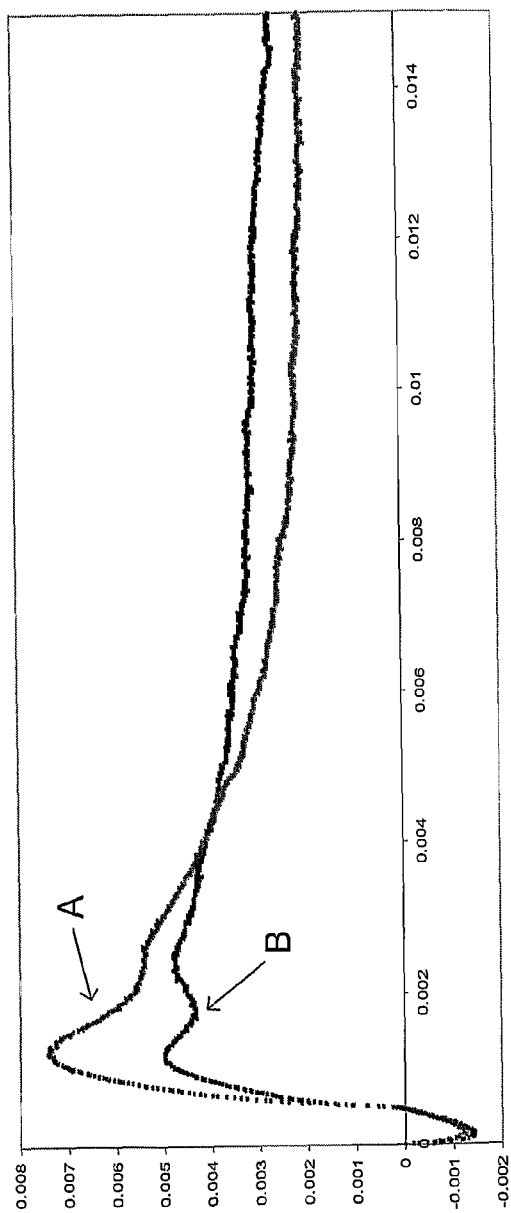

FIGS. 6A & 6B each show the piezoresistive sensor voltages indicative of the deflection amplitude of a flexible member as a function of time in solutions of both brine and water, with respectively a 0% and a 30% mix with glycerol;

FIG. 7 is a schematic diagram of a device in accordance with a further embodiment of the present invention; and FIG. 8 illustrates the relative deflection amplitudes of the devices of FIGS. 1 & 7 as a function of time, following an initial excitation pulse.

Figure 1A:
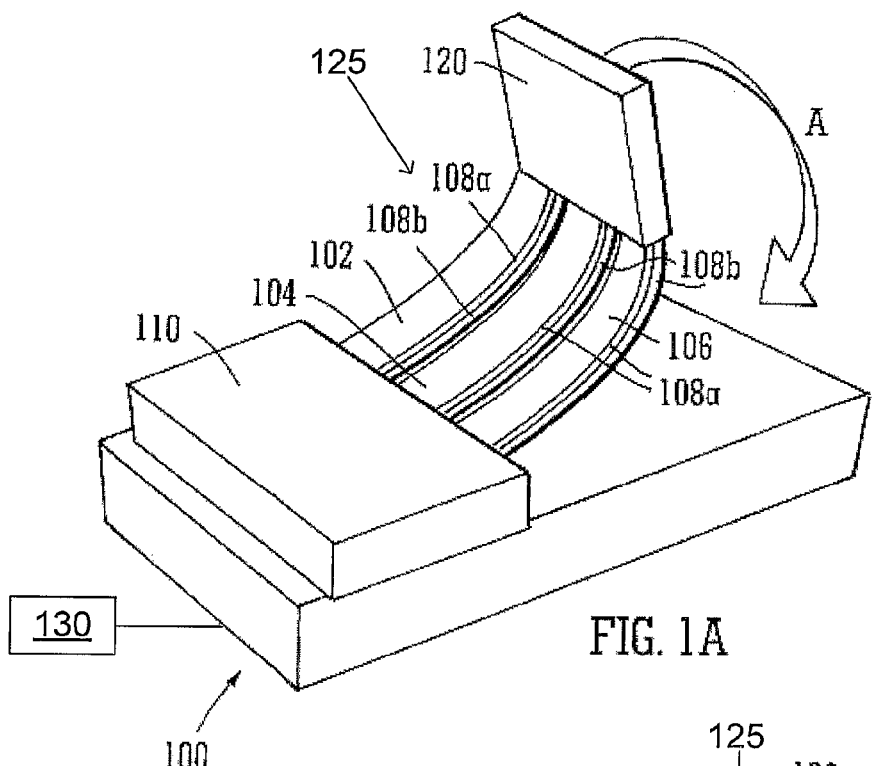
FIGS. 1A & 1B show perspective views of a device having a single flexible member in accordance with an embodiment of the present invention, in a first configuration and a second configuration.
Figure 1B:
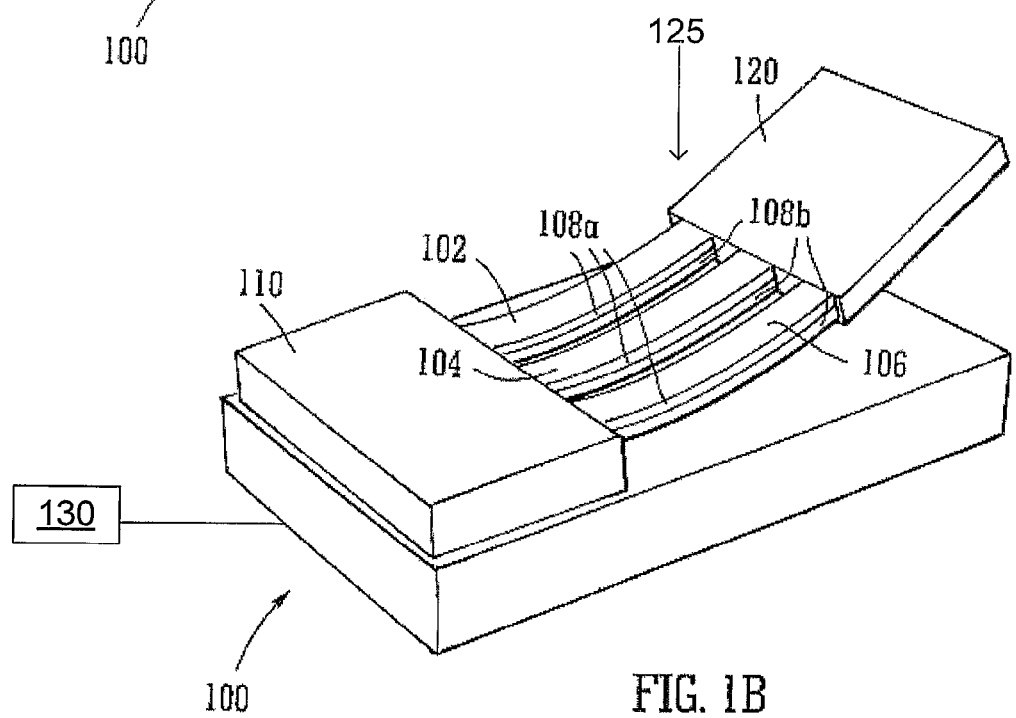

FIGS. 1A & 1B illustrate a device 100 for detecting the properties of a fluid, such as a gas or a liquid, in accordance with an embodiment of the present invention.

The device 100 comprises three flexible elements, 102, 104, 106 coupled to a body region 110.

The first end of each flexible element is connected to the body region 110. The second end of each flexible element, distant from the first, is free to move in relation to the body region. Each flexible element is a bar with a rectangular surface area, with the long side of the rectangle extending from the body region 110. Each flexible element 102, 104, 106 comprises a laminate of at least two layers 108a, 108b.

The materials of each layer have different coefficients of thermal expansion. The layers can be formed of different materials. Alternatively, each of the layers can be formed of the same material, with that material processed in different ways (e.g. stressed in a particular direction and/or coupled to further materials within the flexible elements) such that the layers display different coefficients of thermal expansion. For example, stressing of the materials in different directions can lead to the thermal coefficient of expansion having directional dependence. Thus, if the different layers are formed of the same material, but with the different layers being stressed in different directions, the different layers will effectively have different coefficients of thermal expansion. The first layer may have a thermal expansion coefficient that is 2× (or 5×, or even 10×) the thermal expansion coefficient of the second layer. The difference between the thermal expansion coefficients may be at least $10 \times 10^{-6}/°C$. The layers may be formed of a material having a Youngs modulus less than 10 Gpa.

Suitable materials performing each layer include polymers, polyimides, polyamides and acrylic polymers.

Under application of heat, one layer will expand more than the other for the same rise in temperature, and hence the flexible element being heated will bend in the direction of the material with the lower coefficient of expansion (e.g. to the position shown in FIG. 1A). As the flexible elements cool, one layer will contract to a greater degree than the others for the same decrease in temperature, and hence the flexible element will then unbend in the direction of the material with the greater coefficient of expansion (e.g. as shown in FIG. 1B).

Each of the three flexible elements 102, 104, 106 is of substantially the same length, width and thickness. A coupling member 120 is connected to each of the free ends of the flexible elements 102, 104, 106 (i.e. the second ends of the flexible element, that are distant from the body region 110). Each of the flexible elements may be laterally spaced from adjacent flexible elements i.e. such that there is a gap between each of the flexible elements 102, 104, 106. Such a gap limits thermal conduction between the flexible elements. Typically, the coupling member 120 will also be formed of a thermally insulating material.

Together, the flexible elements 102, 104, 106 and the coupling member 120 form a flexible member 125. The flexible member may have a spring constant of approximately 1 N/m. The flexible member may be 10 microns or more in length. It may be 2 mm or less in length.

The flexible member 125 includes at least one flexible element 102, 104, 106 comprising a heater e.g. an electrical heater element to heat the flexible element 102, 104, 106, so as to result in movement of the flexible member 125. For example, the electrical heater element could be formed of a metal or metal alloy. The heater element may be formed of a material having a substantially uniform resistivity. The electrical heater element could be formed from constantan. A material such as constantan has a relatively low temperature coefficient of resistance i.e. its resistance does not vary significantly with temperature. The electrical heater element may be formed of material (e.g. metal or metal alloy) that is highly conductive and relatively elastic, for example Au, Pt, Cu or similar.

The flexible member 125 also includes at least one flexible element 102, 104, 106 comprising a sensor, to sense and provide a signal indicative of the movement of the relevant flexible element 102, 104, 106 (and hence a signal indicative of the corresponding movement of the flexible member 125). The sensor is arranged to provide a signal indicative of the degree of bending of the flexible element. As described within the prior art, various movement sensors are known, and could all be implemented within embodiments of the present invention. In this particular embodiment, the movement sensor takes the form of a piezoresistive material. A piezoresistive material is one whose electrical resistance changes upon the application of mechanical strain. For example, the piezoresistive material of the sensor could be formed of nichrome, a chrome-copper alloy, Au, Pt or a polymer. The sensor may be formed of constantan, the resistance of which is relatively temperature insensitive. Using a relatively temperature insensitive material such as constantan reduces thermal cross-talk between the heaters and sensors.

The signal output from the sensor can be regarded as comprising a thermal component (due to expansion of the sensor/flexible element with temperature) and a strain component (due to movement of the sensor/flexible element). For measurements of fluid properties such as viscosity, it is desirable to only look at the strain component of the sensor signal in response to the excitation of the flexible member, and hence to minimise the thermal component. The strain component is indicative of the bending motion of the flexible element.

The flexible member 125 may comprise three flexible elements 102, 104, 106, with the central flexible element 104 comprising the sensor, and the two outer flexible elements 102, 106 each comprising a heater to induce movement. Both heaters may be operated simultaneously (e.g. by providing an identical/the same electrical signal to each heater element), for bending the flexible member (including the central flexible element 104 including the sensor) without imparting a twisting motion. The signal from the sensor is then monitored, and subsequently analysed by a processor. The processor provides a signal indicative of the desired fluid property. For example, by analysing the motion of the deflection as a function of time, the viscosity of the fluid within which the flexible member is located can be determined.

The device 100 includes a controller 130. The controller 130 includes a heat controller arranged to supply an electrical pulse to the electrical heater element(s) within the flexible member(s). As will be described below with reference to FIGS. 5A-5D, the pulse may be relatively short, for example less than 8 ms, and in some embodiments less than 5 ms, in duration. The pulse may for example be 100 μs or longer. The pulse may be shorter than 100 μs, for example, at least 50 μs.

The controller 130 may also comprise a processor arranged to receive and process the signal from the sensor, and to thereby determine a value indicative of a property (for example viscosity) of a fluid surrounding the flexible member. The controller 130 is arranged to provide an output signal indicative of the determined property, for example as a function of time.

Possible arrangements of flexible members, sensors and heater elements within flexible elements, will now be described with reference to FIGS. 2-4.

Figure 2:
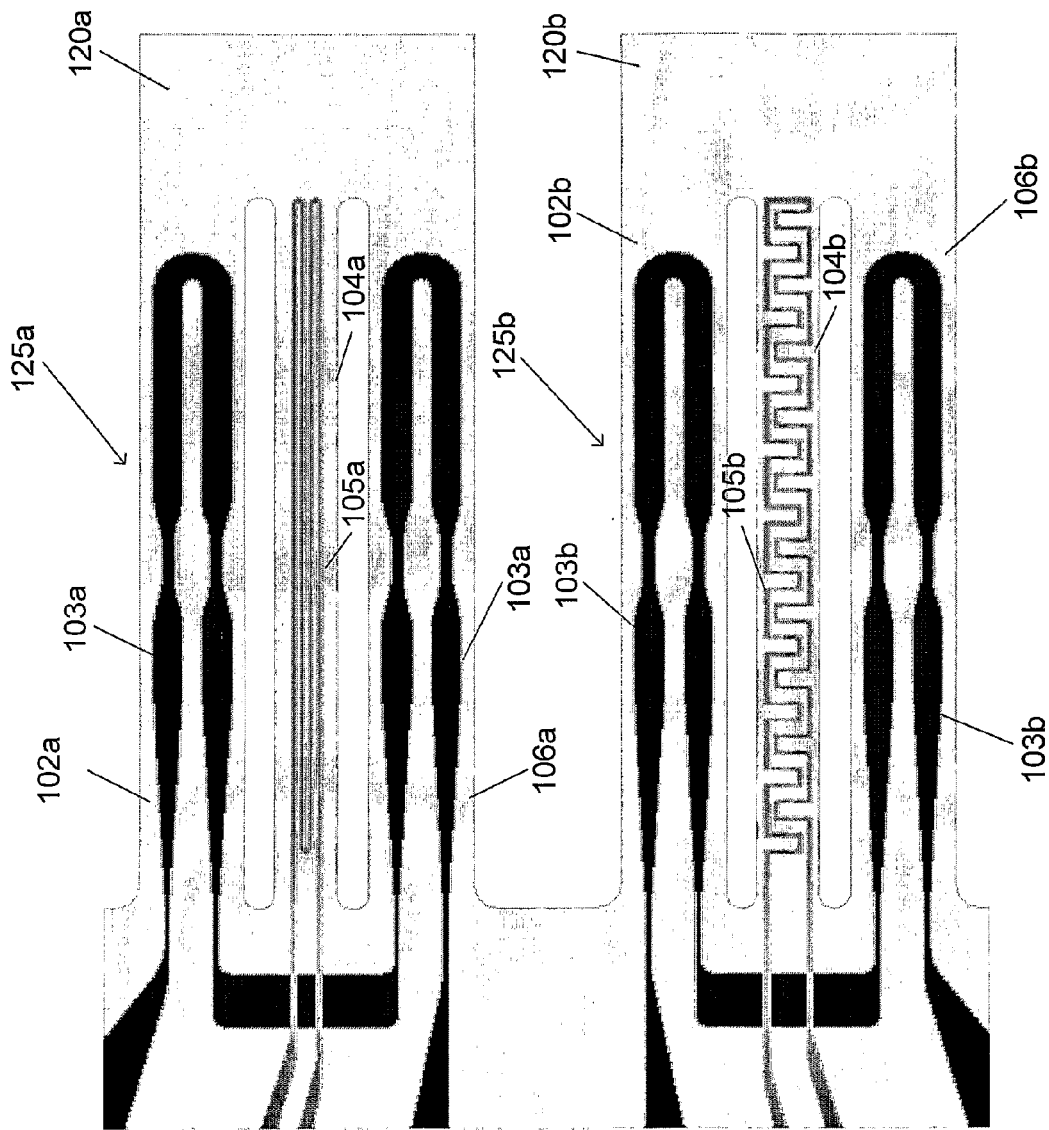
FIG. 2 shows a schematic plan view of a device having two flexible members, indicating the relevant sensor and heating elements.

Instead of the device 100 including one flexible member 125 as shown in FIG. 1, the device 100 may include two flexible members 125a, 125b as shown in FIG. 2. Where this is done, one of the flexible members (125b) acts as a reference.

Each flexible member 125a, 125b corresponds generally to the flexible member 125 illustrated in FIG. 1. The flexible members 125a, 125b are each connected to a single, common body region. In the example shown, the flexible members 125a, 125b are side by side, generally extending within a common plane (e.g. the plane of the sheet of paper indicating the Figure). In an alternative configuration, the flexible members 125a, 125b may extend in parallel planes, overlapping each other e.g. with one flexible member on top of the other flexible member.

In particular, each flexible member 125a, 125b in this embodiment comprises three respective flexible elements (102a, 104a, 106a; 102b, 104b, 106b). A respective coupling member 120a, 120b connects together the flexible elements within each flexible member 125a, 125b.

The outer two flexible elements 102a, 106a; 102b, 106b of each flexible member 125a, 125b comprise integral electrical resistance heater elements 103a, 103b. The heater elements can be formed within one of the two layers of material having different thermal coefficients of expansion, or can be formed between the two layers. The configuration (i.e. shape and location and dimensions) of each heater element formed within every flexible element (102a, 106a, 102b, 106b) is identical. This ensures that every heater element provides a similar heating effect to the relevant respective flexible element i.e. such that both flexible members 125a, 125b experience similar heating effects, and therefore are induced to bend by similar amounts.

It will be seen in FIG. 2 that the electrical heater elements 103a in both the flexible elements 102a, 106a, are connected electrically in series, as are the electrical heater elements 103b in the second flexible member 125b. For convenience, flexible heater elements 103a may also be connected to the electrical heater elements 103b in the second flexible member 125b. Such connectivity facilitates the provision of similar excitation pulses to each heater element i.e. to providing similar levels of power, and pulses of similar shape and duration, to each individual heater element formed on each individual flexible member.

The central flexible elements 104a, 104b each comprise a respective sensor in the shape of a sensor element 105a, 105b. It will be noted that the configurations of the sensor elements 105a, 105b differ. Although each sensor element 105a, 105b extends substantially along the full length of the flexible element, the particular shape of each sensor element 105a, 105b differs. This different configuration is used to provide different functionality. In particular, the sensor element 105a on the first flexible member 125a is more sensitive to strain than the sensor element 105b on the second flexible member 125b. Typically, the second flexible member acts as a reference i.e. with sensor element 105b providing a reference signal.

The reference sensor element 105b is substantially identical to the active sensor element 105a in terms of total material composition and thicknesses/amounts of material. Thus, the sensor elements 105a and 105b will have a similar resistance. Further, as explained below, the sensor elements 105a and 105b will be surrounded by/be a part of flexible elements having substantially the same thermal conductivity (due to the use of additional material 250, as explained below with reference to FIG. 4). Thus, the signal output from the sensor elements 105a & 105b should have substantially the same thermal component. In other words, the thermal components of the signals from sensor elements 105a & 105b should be substantially the same for each sensor.

However, due to the difference in configuration between the sensor elements 105a & 105b (e.g. the footprint or shape of the sensors), the strain components of the respective output signals will be different. In particular, one of the sensor elements 105a is provided so as to have a larger strain component than the other sensor element 105b. These sensor elements may be considered to be an active sensor element 105a and a reference sensor element 105b respectively. Thus, conveniently, the output signal from the reference sensor element 105b can be subtracted from the output signal from the active sensor element 105a, to leave a net signal having substantially only a strain component. In other words, subtracting the output signal of the reference sensor element 105b from the output signal of the active sensor element 105a should minimise (and may neutralise) the thermal component of the net (total) signal, and simply leave a strain component. The signals can conveniently be subtracted by coupling both sensors to appropriate arms of a Wheatstone Bridge configuration, such that the voltage output from the reference sensor element 105b is subtracted from the voltage output from the active sensor element 105a in the Wheatstone bridge configuration.

A common controller (e.g. 130) can be coupled to both flexible members 125a, 125b. The controller is arranged to provide the same electrical pulse to excite (i.e. heat) the heater elements 103a, 103b of each member 125a, 125b. Further, the controller is arranged to process the signals from the sensor elements 105a, 105b, so as to determine the viscosity of each fluid.

Figure 3A:
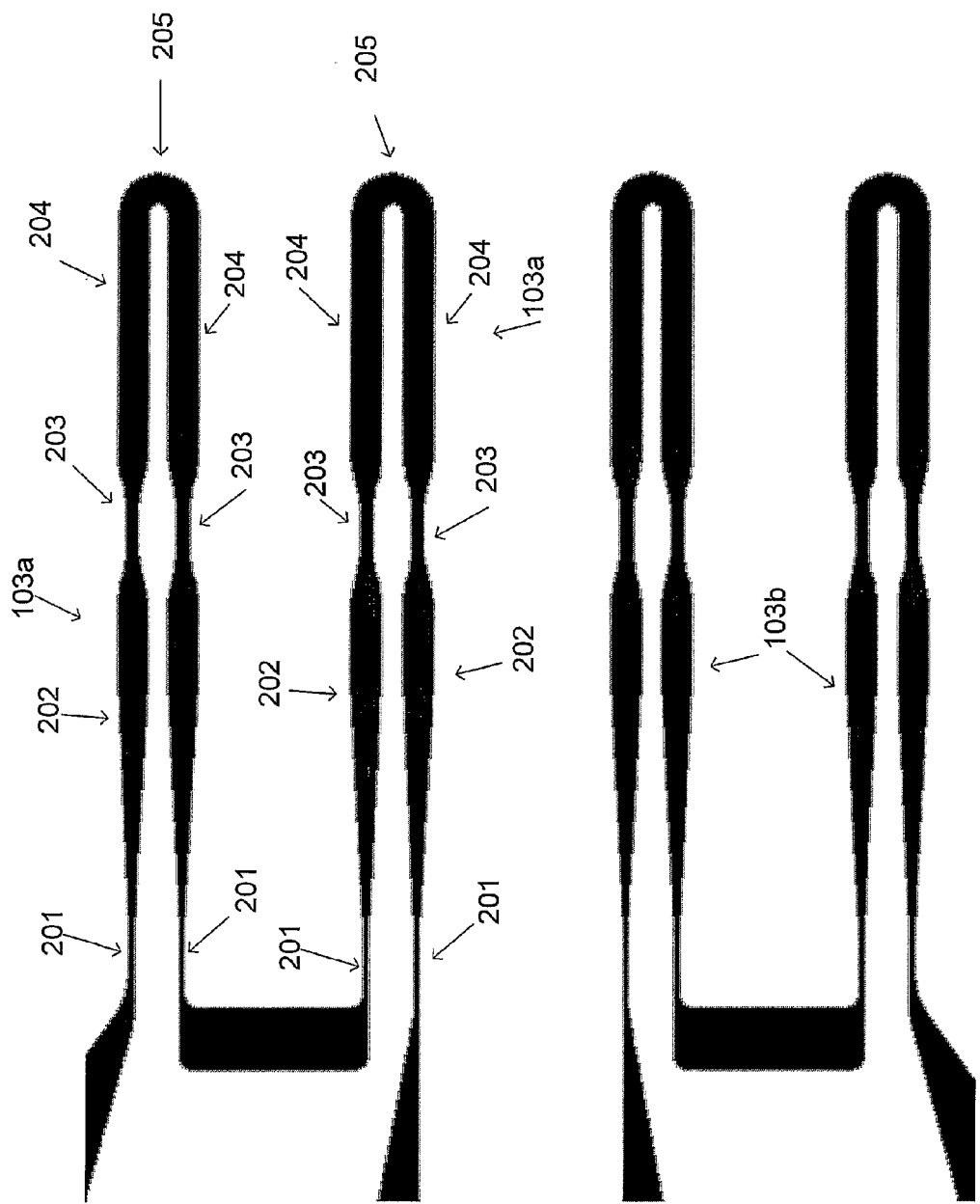
FIGS. 3A & 3B show respectively the configuration of the heating element and the sensors of FIG. 2.

FIG. 3A shows only the heater elements 103a, 103b. Since each heater element 103a, 103b has the same configuration (i.e. size & shape) the description of the configuration will be made with reference to one of the heater elements (103a). However, it should be understood that the same details of configuration apply to the other heater element 103b.

As can be seen from FIG. 2, each heater element extends in a circuit from a position adjacent the first end of the respective flexible element (adjacent the body region) via the second, distant end of the flexible element (i.e. 205), back to the first end. At the first end, the heater element is electrically connected to corresponding electrically conductive portions on the body region (110) of the device, and from there to the controller 130 (e.g. see FIG. 1).

Typically, each heater element will be of uniform thickness, to facilitate forming the elements within a single deposition layer. Typically, the material forming each heater element will also have substantially uniform resistivity. However, the resistance as a function of distance along the heater element is advantageously varied.

The resistance R of a section of electrically conductive material of length 1, cross-sectional area A, can be calculated from the equation:

$$R = \rho l/A$$

where $\rho$ is the resistivity of the material. In other words, the resistance of a section of material is inversely proportional to the cross-sectional area of that section.

The electrical heating element 103a performs two functions. As well as heating the relative flexible element, the electrical heating element 103a also acts as a thermal conductor, spreading thermal energy within the flexible element after the electrical pulse powering the heater element has stopped. Thus, it can be desirable to have a relatively high cross-sectional area heating element, so as to assist with distribution of thermal energy within the flexible element. On the other hand, it can be desirable to have a relatively narrow heating element to provide a high R, so as to ensure that the highest possible amount of thermal energy is dissipated within the heating element, so as to induce bending of the flexible element. Further, the electrical heater element 103a is often formed of a relatively rigid material, such as a metal, which can result in an undesirable relatively stiff layer within the flexible element.

The interplay of all of these parameters, and the performance of the electrical heater element 103a has been improved, compared with prior art devices, by providing a relatively narrow portion 201 of the heater element adjacent the first end, so as to maximise the flexibility and the heating effect within that portion. A further, relatively narrow portion 203 of the heater element is located in an intermediate section/position of the flexible element, so as to again maximise the heating/flexible element flexibility around that position, thus further enhancing the degree to which the flexible element bends upon heating. If desired, a number of such narrowed "waists" of heater element could be provided. To assist in distribution of heat elsewhere within the heater element, these narrower portions 201, 203 are formed between wider portions 202, 204. The width of the heater element tapers from the wider portion to the adjacent narrower portions.

Thus, a relatively large footprint of metallization (e.g. heater element tracks with wider portions) can be provided, so as to allow quick distribution of heat and better response of the cantilevers. Further, narrower portions (201, 203) are provided, reducing the mechanical stiffness at those portions, and increasing the heating effect of those portions.

The term 'narrower portion' is intended to mean that the portion is narrower than the wider portion. Similarly, the term 'wider portion' is intended to mean that the portion is wider than the narrower portion.

In some embodiments, at least some of the functions of the narrower portions 201, 203 may be performed by meandering portions of the heating element track. Meandering portions of the track do not travel directly along the flexible element but bend back and forth, for example in a serpentine manner, so as to provide a greater length of heating element track for a given length of flexible element. This results in a greater degree of heat provided to sections of the flexible element which contain meandering portions. In embodiments comprising meandering portions of heating element track, the cross section of the track may be even along the length of the heating element track.

Figure 3B:
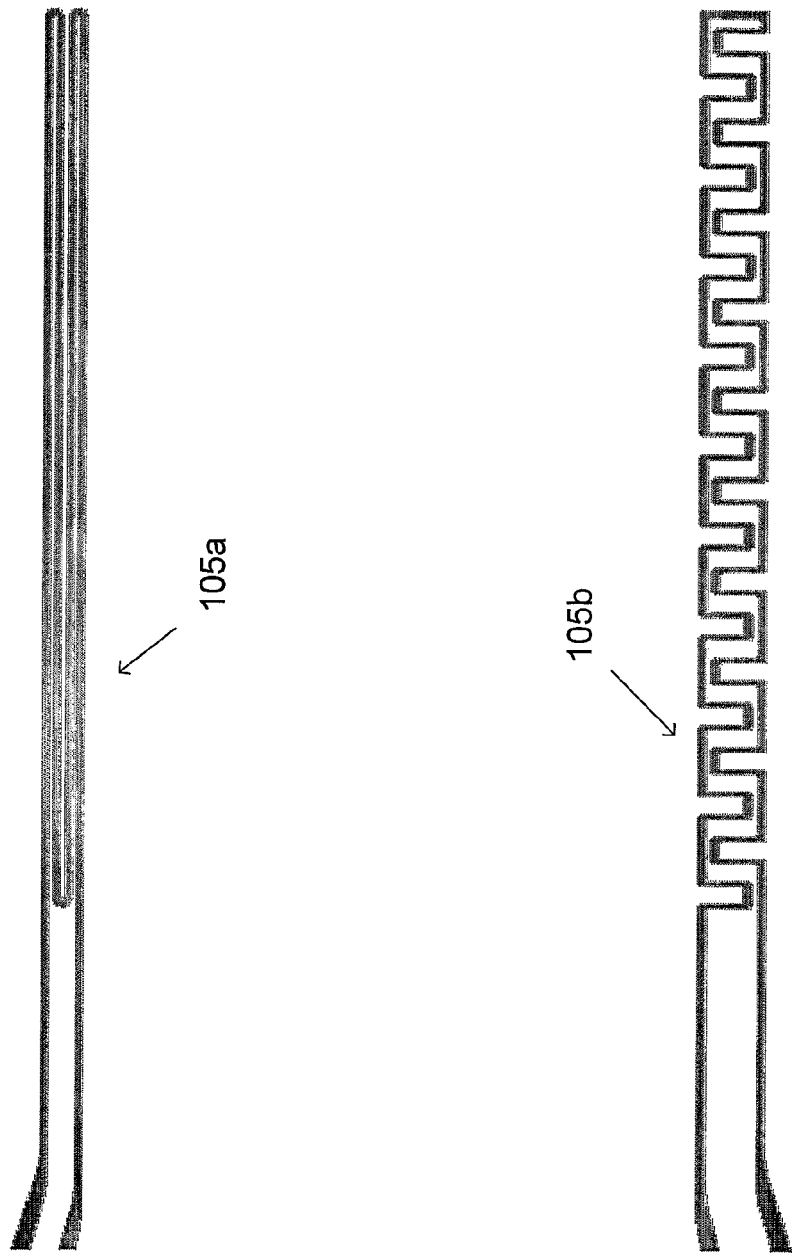

A brief description will now be provided of the configuration of the sensor elements 105a, 105b, with reference to FIGS. 2 & 3B.

Typically, the sensor element 105a is arranged to be more sensitive to longitudinal strain along the flexible element than the reference sensor element 105b. Such sensitivity can be realised by varying the shape, and relative dimensions of the different sensor tracks forming each sensor. Each sensor may be of the same thickness, so as to readily facilitate forming the sensor tracks within each flexible element in a single processing step.

Each sensor element 105a, 105b is formed as an element which extends longitudinally along each flexible element (e.g. flexible elements 104a, 104b). The sensor elements 105a, 105b may extend along the full length of the elements, so as to determine movement along the full length of the element.

However, so as to maximise the sensitivity to linear strain, the sensor element 105a has a greater proportion of its length that extends longitudinally along the flexible element than the corresponding reference sensor element 105b. In the particular configuration shown in FIG. 3B, sensor element 105a comprises a track that can be envisaged as being formed of four longitudinally extending portions, with each longitudinally extending portion being coupled to an adjacent portion at an end. Thus, only at the ends of the longitudinally extending portions are there any transversely extending portions of the track (i.e. portions that do not extend longitudinally along the flexible element).

By way of contrast, the track of the reference sensor element 105b extends in a serpentine manner along the flexible element, with portions extending transversely separated by portions extending longitudinally, such that a greater proportion of the total length of the track extends transverse the flexible element.

Thus, the reference sensor element 105b is less sensitive to longitudinal strain than the sensor element 105a but has a similar thermal sensitivity. In addition, the sensitivity of the reference sensor element 105b to strain can be decreased further by ensuring that the longitudinally extending portions of the track are relatively wide compared with (i.e. wider than) the transversely extending portions (such that the overall portion of signal due to strain is greatly reduced due to the relationship between resistivity and cross-sectional area).

Thus, the active sensor element 105a can be made more sensitive to strain than the reference sensor element 105b. As described above, the output signal from the reference sensor element 105b can be subtracted from the output signal from the active sensor element 105a, resulting in a net output signal that has substantially only a strain component (i.e. without a significant thermal component).

Due to the different sensor elements 105a, 105b having different configurations, the relative distribution of the material forming the sensors will be different within each respective flexible element 104a, 104b. In respect of the particular configuration shown in FIG. 3B, the reference sensor element 105b will be formed of more material than the corresponding active sensor element 105a. Such differences in structure may be undesirable.

It may be desirable that each flexible element (e.g. 104a, 104b) has the same mechanical and thermal properties. Typically, the sensors will be formed of a piezoresistive material e.g. a metal that is a thermal conductor but also relatively rigid. It may therefore be desirable that each flexible element contains the same proportions of materials e.g. the same proportions of metals to non-metals, with approximately the same distribution of such materials. Accordingly, to compensate for the greater material used in reference sensor element 105b, the flexible element 104a comprising the active sensor element 105a is filled with one or more passive portions of additional material 250.

Figure 4:
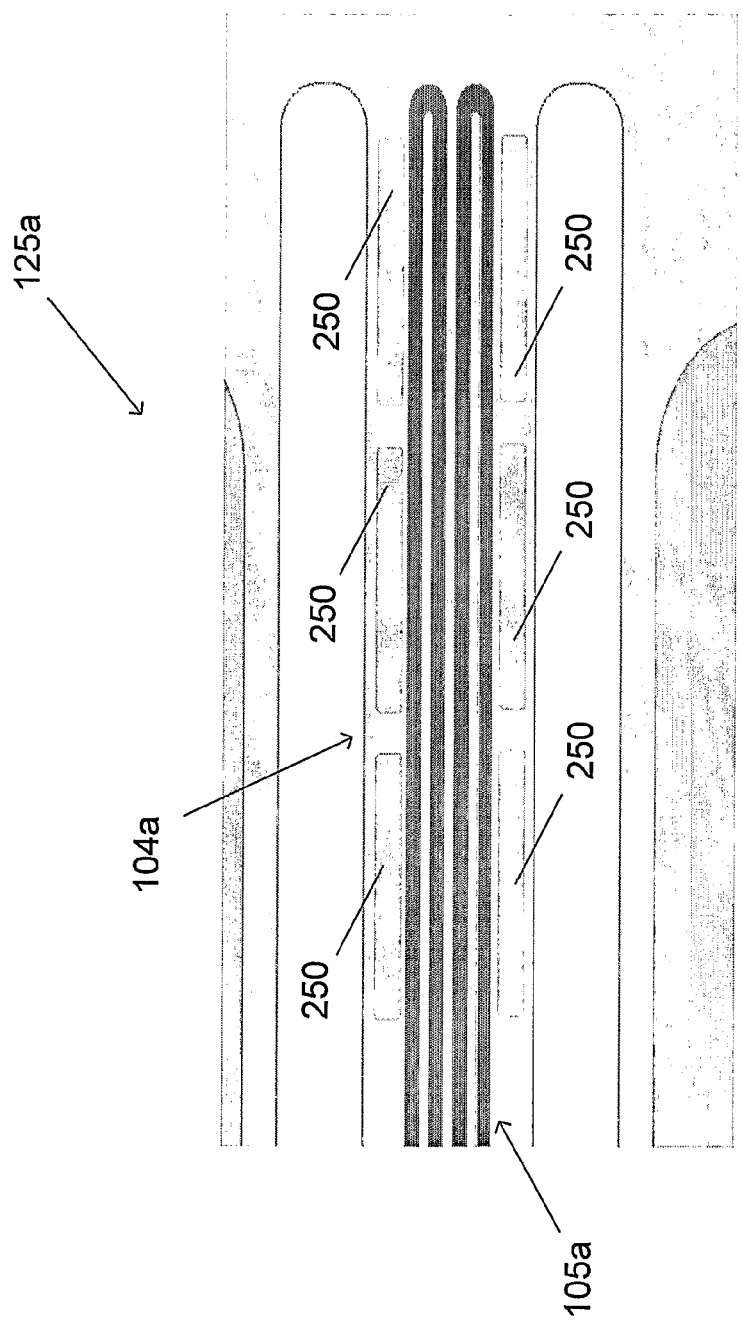
FIG. 4 is a schematic plan view of a flexible member in accordance with an embodiment of the present invention, illustrating the location of additional portions of material.

FIG. 4 shows a close-up view of the flexible element 104a, and indicates how additional portions of material 250 can be distributed along the flexible element 104a, for equalising the distribution in thermal conductivities of the flexible elements 104a, 104b.

The additional portions of material 250 may exhibit similar thermal conductivity to the material of the sensor elements 105a. The additional portions of material may be formed of the same material as the sensor elements 105a (for both ease of construction and also so as to ensure uniform properties). Where this is done, the additional portions of material may also result in a corresponding equalisation of rigidity of both flexible elements. If the additional material 250 is a metal, the additional material 250 may alter the ratio of metallic to non-metallic constituents in the reference flexible element 104a so that the ratio is equal in the two flexible elements 104a, 104b.

As indicated above, the controller 130 is arranged to provide an electrical pulse to the electrical heater element(s), and thereby induce bending of the flexible element(s).

The pulse may be short enough that the pulse ends before bending induced in the flexible element(s) has reached a maximum, or such that a significant mechanical overshoot of the flexible element(s) occurs. The pulse may be short enough that a significant element of mechanical deflection of the flexible element(s) occurs after the pulse has ceased. The mechanical deflection may be sufficiently large so as to be measurable.

The pulse may be such that it induces a deflection of the flexible element(s) which is sufficiently rapid that is causes a measurable amount of mechanical oscillation of the flexible element(s) to occur (these mechanical oscillations are described further below). This may be achieved for example via the pulse being sufficiently short and energetic that it delivers an impulse to the flexible element(s) which is large enough to initiate the measurable amount of mechanical oscillation. The pulse may be sufficiently short that the pulse and subsequent measurement of mechanical oscillation are temporally separate.

The pulse may be a so-called top-hat function, or may approximate such a function. It is not necessary to excite the flexible element(s) using for example a sine-wave electrical signal at a resonant frequency, due to the flexibility of the flexible element(s) (compared with for example a probe which is fabricated from silicon). A top-hat function or approximation thereof includes a variety of different frequencies, and therefore may assist in for example exciting measurable mechanical oscillations in the flexible elements. A duty cycle of for example 5%, 10% or 20% may be used. The pulses may be temporally separate. Rather than a regular duty cycle, an irregular amount of time may be left between pulses. The frequency of the electrical pulses may be at least two orders of magnitude less than the resonant frequency of the flexible element(s), and may be for example 100 Hz or less.

The pulse may for example be less than 8 ms in duration, 5 ms in duration or less, 2 ms in duration or less, 1 ms in duration or less, or 0.5 ms in duration or less.

When delivering a predetermined required amount of energy using a pulse, if the pulse is shortened in duration then the intensity (i.e. the peak voltage) of the pulse must be increased. If the pulse is too short, then the intensity of the pulse may be so high that it causes damage to the heating element and/or to the surrounding flexible element. This may be avoided by using a pulse which is long enough to deliver sufficient energy to the heating element(s) to cause a required degree of bending of the flexible element(s) without causing damage to the heating element. The pulse may for example be at least 100 μs in duration, may be at least 250 μs in duration, and may be 0.5 ms in duration. The pulse may be at least 50 μs in duration, for example in the case that the flexible element is surrounded by a gas.

Figure 5A:
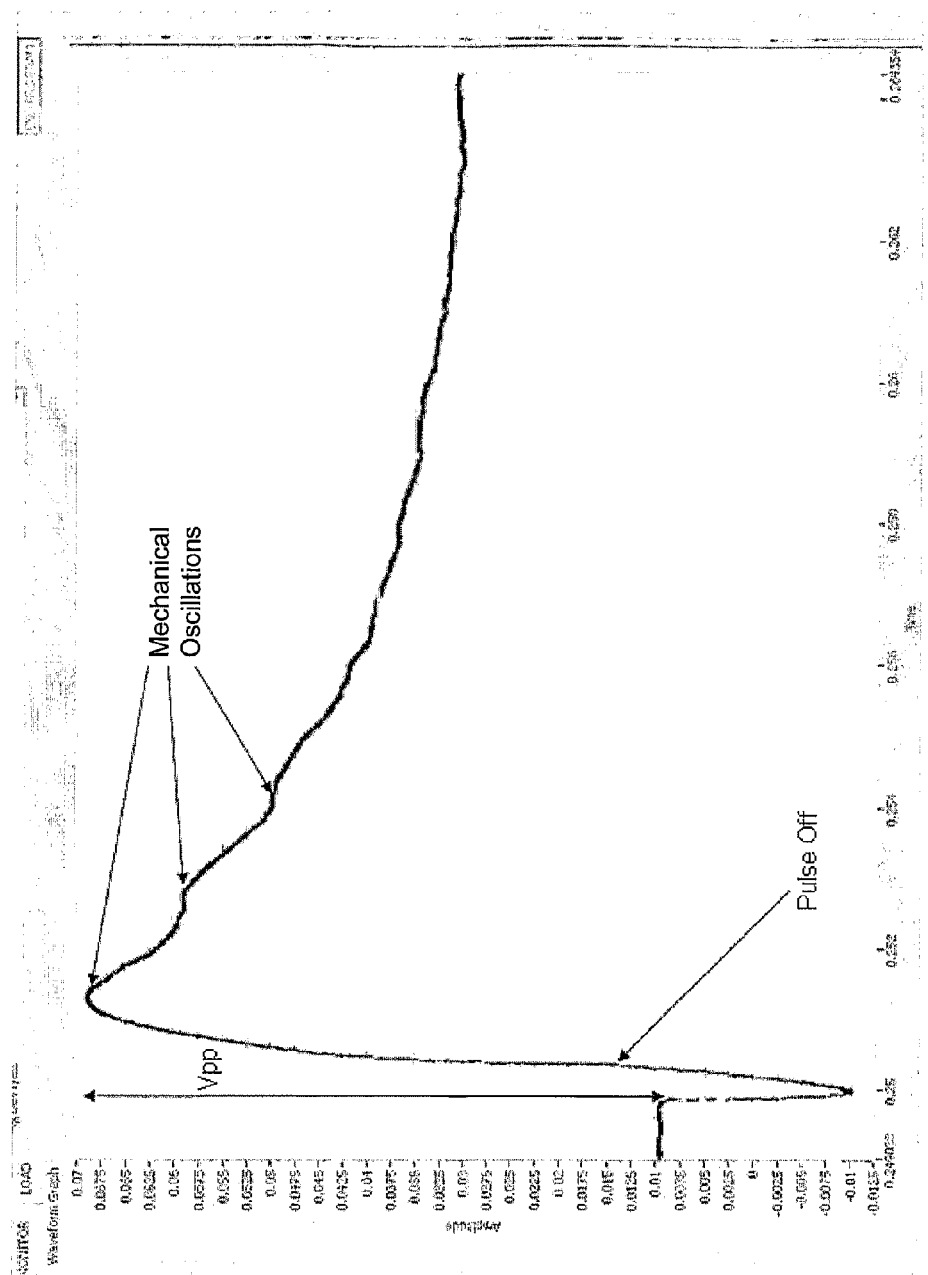
FIGS. 5A-5D are graphs each illustrating the deflection amplitude of a flexible member as a function of time in response to a pulse of the same predetermined total energy, at respective pulse durations of 0.5 ms, 1.0 ms, 2.0 ms, and 4.00 ms respectively.
Figure 5B:
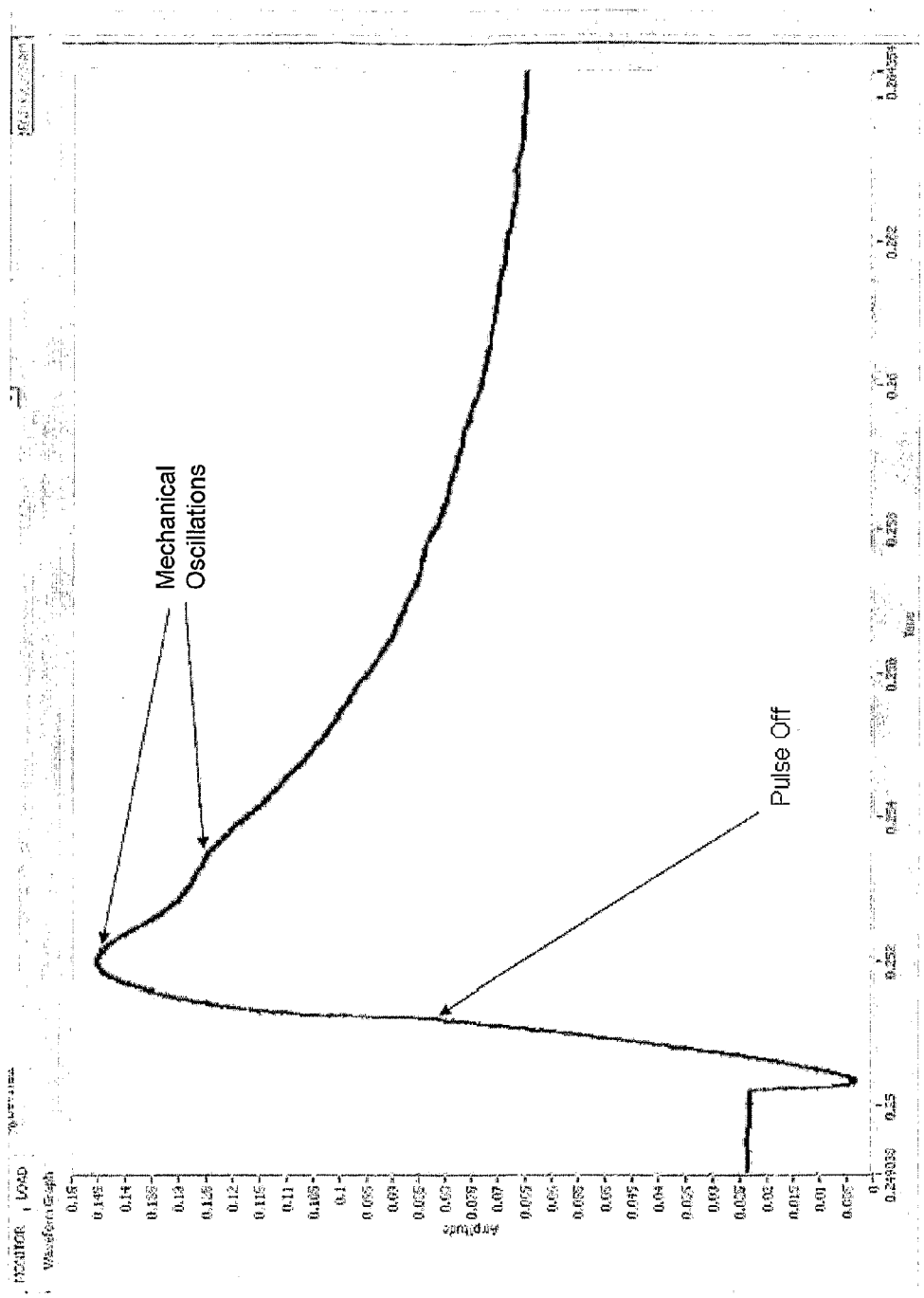
Figure 5C:
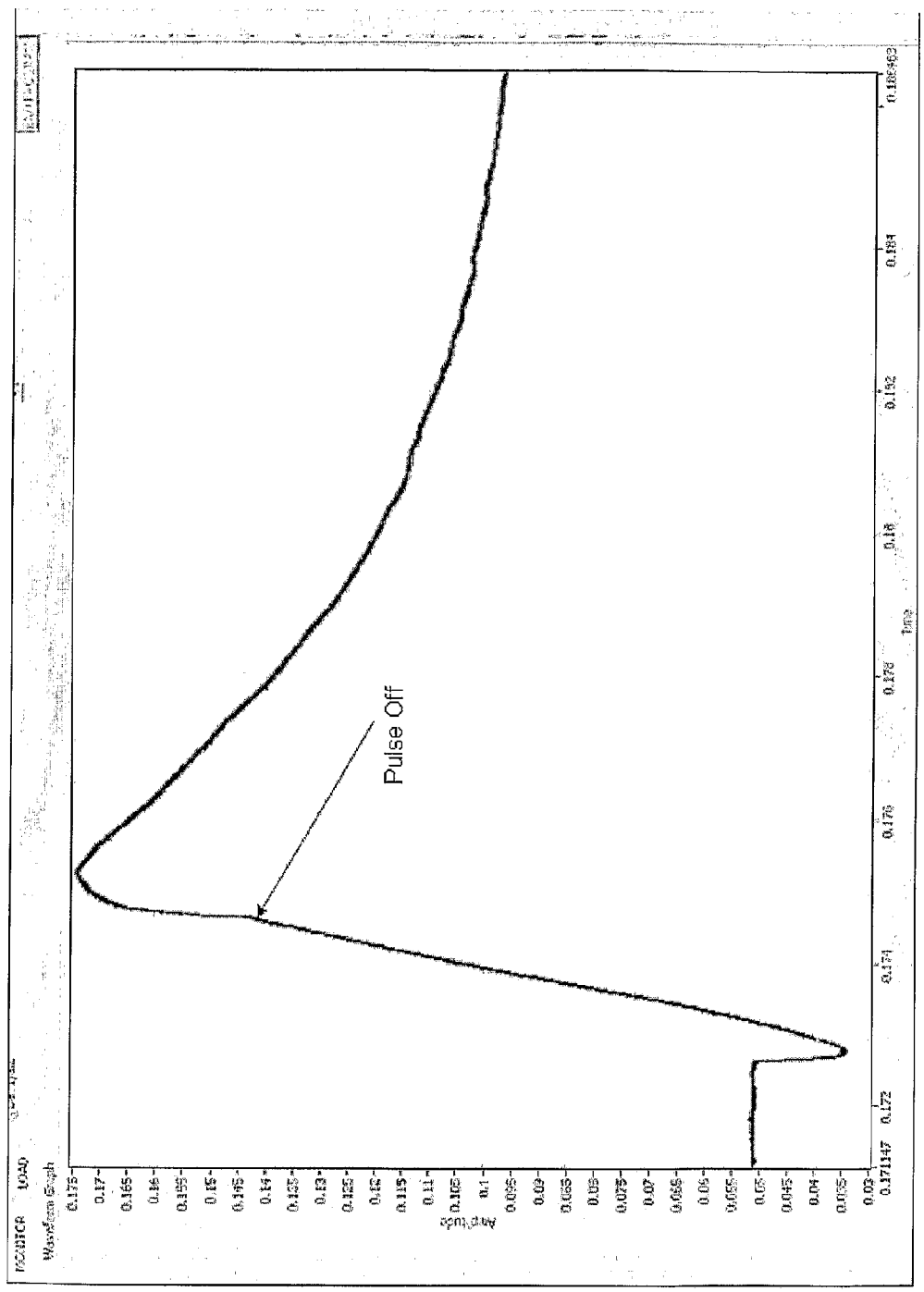
Figure 5D:
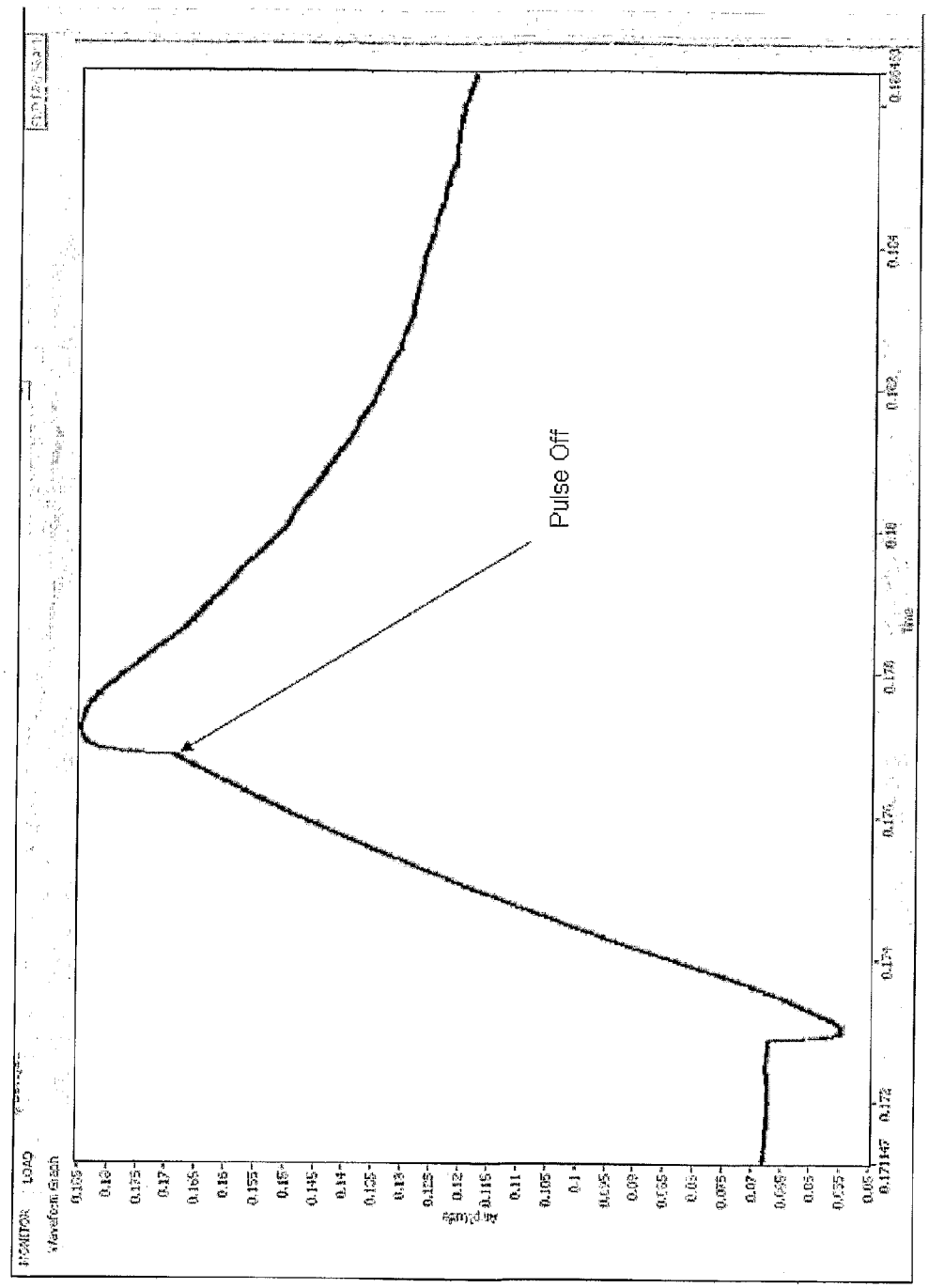

FIGS. 5A-5D show the effects of utilising pulses of different duration, with FIG. 5A showing a 0.5 ms pulse, FIG. 5B showing a 1.0 ms pulse, FIG. 5C showing a 2.0 ms pulse, and FIG. 5D showing a 4.0 ms pulse. In each case the applied pulse voltage is adjusted, so as to ensure that the total pulse energy was the same.

The minimum energy supplied to the heating element may be 50 μJ, for example when the probe is placed into fluid of approximately 1 centipoise. The maximum energy supplied to the heating element may be 60 μJ for example for a fluid of approximately 1 centipoise. For more viscous fluids, the minimum or maximum energy may be higher and for less viscous fluids the minimum or maximum energy may be lower. The minimum energy should be sufficient to cause measurable mechanical overshoot in the flexible element. The maximum energy should not be sufficient to damage the flexible element or to mask a mechanical overshoot. The minimum energy supplied to the heating element may be 1 μJ or may be 100 μJ. The maximum energy supplied to the heating element may be 10 μJ, 150 μJ or may be 250 μJ.

FIGS. 5A-5D show the responses of the measurement sensor within the flexible element. The device 100 utilised to perform these measurements was of the type illustrated in FIG. 1. FIGS. 5A-5D show a voltage amplitude resulting from the change in electrical resistance of the sensor (with the sensor forming part of a Wheatstone Bridge). Thus, the amplitude is indicative of the deflection of the flexible element containing the sensor. Within each Figure, it will be observed that an initial negative going portion of the signal is present. The start of this initial negative going portion corresponds to the relevant electrical pulse. In each Figure, the time period at which the pulse stops is also indicated.

It is believed that the initial negative going portion of each graph is due to electronic parasitic effects and an initial buckling of the flexible element prior to the flexible element then bending (as indicated by the subsequent increase in voltage amplitude). The voltage amplitude rises to a peak, which corresponds to the maximum deflection of the flexible element i.e. the maximum degree of bending of the flexible element caused by the heat pulse. The flexible element then relaxes, i.e. it unbends, with a subsequent relatively slow decrease in amplitude.

It will be observed that, for shorter pulses, there is a corresponding larger mechanical overshoot. The term 'mechanical overshoot' refers to where the flexible element continues to bend after the electrical pulse has ended. Mechanical overshoot is bending of the flexible element due to mechanical inertia of the flexible element until the maximum deflection point (peak amplitude) is reached. This effect is most pronounced for the 0.5 ms and 1.0 ms electrical pulses, but is present to a lesser extent for the 2.0 and 4.0 ms electrical pulses.

The 0.5 ms and 1.0 ms electrical pulses give rise to a measurable amount of mechanical oscillation (labelled as 'mechanical oscillation' in the Figures). The mechanical oscillation is a small amplitude oscillation which is superimposed on the longer time period curve (similar to a decay curve) formed as the flexible element unbends and returns to its original configuration. The mechanical oscillation occurs as a consequence of the flexible element having been excited by a pulse (any structure will experience mechanical oscillations if excited by a pulse). Although some mechanical oscillation may occur when the 2.0 ms and 4.0 ms electrical pulses are used, the magnitude of these oscillations is not sufficient for them to be visible in FIGS. 5C and 5D, and they may not be measurable.

Both the mechanical overshoot and the mechanical oscillation are useful because they provide additional parameters/functions that may be utilised to determine the viscosity (or other parameter of the fluid). This is in addition to the relatively long period decay-like function which occurs as the flexible element unbends. It will be observed that the mechanical overshoot is greater (in relation to the total amplitude) for short electrical pulses, and in addition that the mechanical oscillation is more pronounced for shorter pulses than for longer pulses. Thus, it may be desirable to use pulses which are sufficiently short to give rise to a measurable mechanical overshoot and/or a measurable mechanical oscillation.

The example pulse durations mentioned further above may be of use when the probe is placed in a fluid of for example 1 centipoise. However, other pulse durations may be appropriate when the probe is placed in a fluid having a different centipoise (the flexible elements will behave differently in different fluids).

The profile of the measured mechanical overshoot will be different in different fluids. In addition, the time period and amplitude of the mechanical oscillation will be different in different fluids. Measurement of these may therefore be used to obtain information about a fluid. For example, the peak of the mechanical overshoot will occur later in a fluid if that fluid is more viscous. In addition, the peak of the mechanical overshoot will be less pronounced if the fluid is more viscous. In this regard, both the size and the quality of the peak may be measured. Furthermore, the time period of the mechanical oscillations will be longer if the fluid is more viscous, and the amplitude of the mechanical oscillations will be less.

Parameters relating to the time constants in the rising portion of the mechanical overshoot, the period of the mechanical oscillation, or the amplitude of the mechanical oscillation, can be determined by standard numerical fitting techniques. These parameters may be used to provide an indication of properties of the fluid. For example, the parameters will vary depending upon the viscosity of the fluid, and can thus be used to monitor the viscosity of the fluid over time. Using a plurality of such parameters may increase the accuracy of the viscosity measurement (or measurement of some other property of the fluid), since they may allow averaging and/or cross-checking of the measurement. Parameters such as the profile of the mechanical overshoot or the time period and amplitude of the mechanical oscillation may be measured more quickly than the time period for bending/unbending of the flexible element, thereby allowing a better indication of the instantaneous viscosity of the fluid to be determined.

FIGS. 6A and 6B illustrate how the response functions vary for different fluids. Both Figures show the voltage amplitudes of a sensor when a 0.5 ms electrical pulse is applied to a heater, resulting in the bending and subsequent unbending of the flexible member containing the sensor. Both FIGS. 6A & 6B show the responses in a water medium (W) and a brine (B) medium (i.e. a saltwater solution). FIG. 6A illustrates the response profiles in pure solutions of water and brine, whilst FIG. 6B indicates the results when the solutions contain 30% glycerol (i.e. are relatively viscous compared to the solutions in FIG. 6A).

The response curves differ between the two Figures. The more viscous medium (Figure B) gives rise to a slower rise time. This is manifest by the peak of voltage amplitude occurring at a later time than the peak of voltage amplitude in the less viscous medium (FIG. 6A), and by time constants in the rising portion of the mechanical overshoot being longer. In addition, the mechanical oscillations which occur in the more viscous medium (FIG. 6B) have a longer period and a lesser amplitude than the mechanical oscillations which occur in the less viscous medium (FIG. 6A).

FIGS. 6A and 6B also demonstrate that the sensor is capable of distinguishing between the water medium (W) and the brine medium (B). The peak of voltage amplitude in the brine medium occurs at a later time than the peak of voltage amplitude in the water medium (in both FIGS. 6A and 6B). In addition, the mechanical oscillations which occur in the brine medium have a longer period than the mechanical oscillations which occur in the water medium. Both the shift of the peak of voltage amplitude and the change of the period of the mechanical oscillations indicate that the brine medium is more viscous than the water medium. The amplitude of the mechanical oscillations which occur in the brine medium may be slightly less than the amplitude of mechanical oscillations which occur in the water medium, although curve-fitting analysis would be needed in order to determine whether this is definitely the case.

The above embodiments are described by way of example only, and various alternatives will be apparent to the skilled person as falling within the scope of the present invention.

For example, embodiments have been described with reference to particular arrangements of flexible elements within flexible members. It should be appreciated that the aspects of the invention relating to the electrical pulse, and the shape of the heater tracks, can be implemented in an embodiment in which the device only includes a single flexible element (i.e. a single flexible member). Moreover, any desirable combination may be made of any of the aspects of the invention, such as those relating to the electrical pulse, heating tracks and reference flexible element.

An example of such a device is illustrated in FIG. 7. The device 10 includes a flexible element 25, within which are disposed both a heater element 3 and a sensor element 5. The general concept of such a flexible element device may be the same as that disclosed within PCT/GB2004/005079, the contents of which are incorporated herein by reference. However, the response of the device illustrated with respect to FIGS. 1-4 (in which the device includes a flexible member, with discrete flexible elements for sensing and heating) may provide better results than the device configuration illustrated in FIG. 7. For example, FIG. 8 illustrates a response curve A for the device of FIG. 1, and a response curve B for the device of FIG. 7. It will be observed that the response curve A in FIG. 8 has a higher peak. This higher peak would enable easier fitting of parameters so as to determine the properties of the fluid in which the relevant flexible element(s) has been immersed.

The flexible element described herein can have similar properties to the flexible element described in PCT/GB2004/005079. For example, the movement of the end of the flexible element can be over a distance between 30 micron and 650 micron. Equally, the movement can have a different range e.g. the movement can be over a range of between 1 micron and 30 micron, or between 1 micron and 650 micron.

Within the above described embodiments, the flexible elements have been described as being alongside each other i.e. with each element side by side generally extending within a common plane. However, the device could be formed with the flexible elements extending in parallel planes e.g. stacked one on top of the other. Such flexible elements may be formed as part of a single flexible member. For example, a flexible member could be formed in which a first flexible element including a respective sensor extends at a first position (e.g. first level or "height") within the flexible member, and a second flexible element having a respective sensor extends at a different position within the same flexible member. For example, a reference sensor could be placed at a position within the flexible member that is less sensitive to strain than the other sensor. For example the reference sensor may be placed close to the neutral axis of the flexible member, such that the reference sensor does not experience as much bending as the other sensor. Thus, the reference sensor would experience less strain than the other sensor (e.g. the active sensor).

In the above described embodiments the probe has been arranged such that flexible element becomes more bent when it is heated (see for example FIG. 1). However, the probe may be arranged such that it starts off with a pronounced bend, and becomes less bent when it is heated. In this context, the term 'bending' as used above may be interpreted as meaning that the flexible element is moving away from an equilibrium configuration to a non-equilibrium configuration, and does not necessarily mean that the flexible element is becoming more bent.

The invention claimed is:

1. A device for detecting a property of a fluid, comprising: a body region; a first flexible element having a first end and a second end, said first end being fixedly located on said body region; a second, reference flexible element having a first end and a second end, said first end being fixedly located on said body region; each flexible element comprising at least a first layer having a first coefficient of thermal expansion and a second layer having a second, different coefficient of thermal expansion, and a respective sensor arranged to provide a signal indicative of the movement of the respective flexible element, wherein the sensor of the reference flexible element has a different configuration than the sensor of the first flexible element, with at least one of the flexible elements including at least one additional portion of material for substantially equalising the thermal conductivity distribution of said flexible elements.

2. A device as claimed in claim 1, wherein the thermal conductivity of said at least one additional portion of material is approximately equal to the thermal conductivity of the sensors.

3. A device as claimed in claim 1, wherein said at least one portion is formed of the same material as the sensors.

4. A device as claimed in claim 1, wherein said sensors are formed of a thermal conductor.

5. A device as claimed in claim 1, wherein the sensor of the second, reference flexible element is configured to be less sensitive to mechanical strain caused by bending of the respective element than the sensor in the first flexible element.

6. A device as claimed in claim 1, wherein the first flexible element is located within a first flexible member, and the second flexible element is located within a separate second flexible member.

7. A device as claimed in claim 1, wherein the first and second flexible elements are located within a single flexible member.

8. A device as claimed in claim 1, wherein said sensor comprises constantan.

9. A device as claimed in claim 1, further comprising a processor arranged to process the signal from the sensor of the first flexible element, to provide a signal indicative of the viscosity of a medium surrounding said first flexible element.

10. A device as claimed in claim 1, wherein each sensor comprises a metal.

11. A device as claimed in claim 10, wherein said at least one additional portion of material is also formed of a metal, and the ratio between the metal and non-metal constituents of each flexible element is substantially the same.

12. A device for detecting a property of a fluid, comprising: a body region; a first flexible element having a first end and a second end, said first end being fixedly located on said body region, the flexible element comprising at least a first layer having a first coefficient of thermal expansion and a second layer having a second, different coefficient of thermal expansion, and an electrical heater element arranged to heat the flexible element to induce bending of said flexible element, wherein the resistance of a first portion of the heater element adjacent the first end is greater than the resistance of a second portion of the heater element further from the first end, such that in use a first section of the flexible element comprising the first portion of the heater element receives more heat per unit time from the heater element than a second section of the flexible element comprising the second portion of the heater element, the second section having about equal dimensions to the first section.

13. A device as claimed in claim 12, wherein said first portion is located in an intermediate section of the flexible element between the first end and the second end.

14. A device as claimed in claim 12, wherein the heater element is formed of a material having a substantially uniform resistivity.

15. A device as claimed in claim 12, wherein said first flexible element has a spring constant of less than about 1 N/m.

16. A device as claimed in claim 12, wherein the first flexible element is between about 10 microns and about 2 mm in length from said first end to said second end.

17. A device as claimed in claim 12, wherein the difference between the thermal expansion coefficients of said layers is at least about $10 \times 10^{-6}/°C$.

18. A device as claimed in claim 12, wherein the ratio between the thermal expansion coefficient of the first layer and the second layer is at least about 10.

19. A device as claimed in claim 12, wherein said layers are formed of materials having a Youngs modulus less than about 10 GPa.

20. A device as claimed in claim 12, wherein said first portion is at the first end of the flexible element.

21. A device as claimed in claim 20, wherein at least a further portion of the heater element is located in an intermediate section of the flexible element between the first end and the second end, has a smaller cross-section than the second portion of the heater element.

22. A device as claimed in claim 12, wherein said first portion of the heater element has a smaller cross-section than the second portion of the heater element.

23. A device as claimed in claim 22, wherein said first portion of the electrical heater element is longer than the second portion of the electrical heater element.

24. A device as claimed in claim 22, wherein the heater element tapers from a larger portion cross-section to a smaller portion cross-section.

* * * * *